United States Patent [19]

Zimmerman

[11] Patent Number: 4,742,168
[45] Date of Patent: May 3, 1988

[54] ANTI-CAKING AGENT FOR TRIETHYLENEDIAMINE

[75] Inventor: Robert L. Zimmerman, Austin, Tex.

[73] Assignee: Texaco Inc., White Plains, N.Y.

[21] Appl. No.: 891,087

[22] Filed: Jul. 31, 1986

[51] Int. Cl.$^4$ ............................................. C07D 487/00
[52] U.S. Cl. ................................... 544/351; 544/352; 252/384; 564/505
[58] Field of Search ................ 544/351, 352; 252/384; 564/505

[56] References Cited

U.S. PATENT DOCUMENTS

| | | | |
|---|---|---|---|
| 2,937,176 | 5/1960 | Herrick | 544/351 |
| 2,977,363 | 3/1961 | Farkas et al. | 544/351 |
| 2,977,364 | 3/1961 | Mascioli | 544/351 |
| 2,985,658 | 5/1961 | Krause | 544/351 |
| 3,166,558 | 1/1965 | Mascioli | 544/351 |
| 4,345,079 | 8/1982 | Hyman et al. | 544/351 |
| 4,356,020 | 10/1982 | Grunert et al. | 252/384 |
| 4,559,384 | 12/1985 | Nomura et al. | 252/384 |
| 4,628,092 | 12/1986 | Takahashi et al. | 544/351 |

Primary Examiner—Glennon H. Hollrah
Assistant Examiner—John A. Sopp
Attorney, Agent, or Firm—Jack H. Park; Kenneth R. Priem

[57] ABSTRACT

The use of certain oxyalkyl amines as anti-caking agents for triethylenediamine (TEDA) is disclosed. The anti-caking agent comprises polyoxypropylene amines or their amides, the amines having the formula:

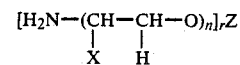

wherein X is hydrogen, a methyl radical or an ethyl radical, Z is a hydrocarbon radical having from 2 to 5 carbon atoms forming from 2 to 4 external ether linkages; n is a number from 1 to about 40 and r is a number from 2 to 4.

7 Claims, No Drawings

ANTI-CAKING AGENT FOR TRIETHYLENEDIAMINE

BACKGROUND OF THE INVENTION

Triethylenediamine (TEDA) is a well known catalyst used in the manufacture of polyurethane products. Triethylenediamine is also known as 1,4-diazabicyclo(2.2.2)octane. Many methods are known for its commercial production; for example, U.S. Pat. Nos. 2,937,176; 3,166,558; 2,985,658; 2,977,364 and 2,977,363.

However, TEDA once isolated is hygroscopic. Therefore, upon storage the purified commercial product forms a hard crust at the surface which will become a thicker and thicker crust when stored for longer periods. This property makes it difficult to use since it is not a free-flowing powder once the crust is formed.

U.S. Pat. No. 4,345,079 discloses and claims the use of polyethylene glycols, glycol esters, glycol ethers and amino alcohols to improve the crusting problem. This patent describes the improved property as scoopability. Among the preferred additives mentioned in the '079 patent are polyethylene glycols and glycol esters.

SUMMARY OF THE INVENTION

The invention is a method for imparting anti-caking properties to TEDA which comprises admixing with TEDA an effective amount of an additive comprising polyoxyalkylene amines or their amides, the amines having the formula:

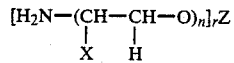

wherein X is hydrogen, a methyl radical or an ethyl radical, Z is a hydrocarbon radical having from 2 to 5 carbon atoms forming from 2 to 4 external ether linkages; n is a number from 1 to about 40 and r is a number from 2 to 4.

DESCRIPTION OF THE PREFERRED EMBODIMENTS

The additive may be mixed with TEDA in any conventional manner effective to disperse the additive throughout the TEDA.

The additives preferred for this invention may be depicted by the formula:

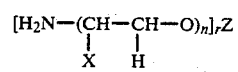

wherein X is hydrogen, a methyl radical or an ethyl radical, Z is a hydrocarbon radical having from 2 to 5 carbon atoms forming from 2 to 4 external ether linkages; n is a number from 1 to about 40 and r is a number from 2 to 4. The most preferred polyoxyalkylene polyamines are the polyoxypropylene diamines wherein X is a methyl radical, n is a number from 2 to 17, Z is a 1,2-propylene radical and r is about 2 or 3. These polyoxyalkylene polyamines can be prepared by known methods as disclosed in U.S. Pat. Nos. 3,236,895 and 3,654,370.

Also useful are mono oxyalkylene polyamines. It has been found that the oxypropylene amines are useful while oxyethylene amines have not performed well.

The range of concentration of the additive by weight percent based on the TEDA is from about 0.1 to about 2.0. It is preferred to use from about 0.8 to about 1.2.

The usefulness of the invention is depicted below where TEDA was blended with the additive, then the mixture was aged at 49° C. After aging, the blends were judged to see if a crust had formed and if they were scoopable.

TABLE I

|  | 1 | 2 | 3 | 4 | 5 | 6 | 7 | 8 | 9 | 10 |
|---|---|---|---|---|---|---|---|---|---|---|
| Triethylenediamine | 125 | 125 | 125 | 125 | 125 | 125 | 125 | 125 | 125 | 125 |
| JEFFAMINE ® D-230 | — | 1.25 | — | — | — | — | — | — | — | — |
| Diacetate of JEFFAMINE D-230 | — | — | 1.25 | — | — | — | — | — | — | — |
| JEFFAMINE D-400 | — | — | — | 1.25 | — | — | — | — | — | — |
| JEFFAMINE D-2000 | — | — | — | — | 1.25 | — | — | — | — | — |
| JEFFAMINE T-403 | — | — | — | — | — | 1.25 | — | — | — | — |
| JEFFAMINE ED-600 | — | — | — | — | — | — | 1.25 | — | — | — |
| JEFFAMINE ED-900 | — | — | — | — | — | — | — | 1.25 | — | — |
| JEFFAMINE ED-2001 | — | — | — | — | — | — | — | — | 1.25 | — |
| JEFFAMINE M-1000 | — | — | — | — | — | — | — | — | — | 1.25 |
| Days aged at 49° C. | 30 | 30 | 30 | 29 | 29 | 29 | 29 | 29 | 29 | 29 |
| Scoopable | no | yes | yes | yes | yes | yes | no | no | no | no |

The JEFFAMINE products that contain only propylene oxide worked well, while those containing ethylene oxide did not.

When No. 2, 3, 4, 5 and 6 were blended 1:2 with dipropylene glycol clear solutions resulted.

JEFFAMINE D-230 - a polyoxypropylene diamine of approx. 230 mol. wt.
JEFFAMINE D-400 - a polyoxypropylene diamine of approx. 400 mol. wt..
JEFFAMINE D-2000 - a polyoxypropylene diamine of approx. 2000 mol. wt.
JEFFAMINE T-403 - a polyoxypropylene triamine of approx. 400 mol. wt.
JEFFAMINE ED-600 - a polyoxyethylene-polyoxypropylene diamine of approx. 600 mol. wt.
JEFFAMINE ED-900 - a polyoxyethylene-polyoxypropylene diamine of approx. 900 mol. wt.
JEFFAMINE ED-2001 - a polyoxyethylene-polyoxypropylene diamine of approx. 2000 mol. wt.
JEFFAMINE M-1000 - a polyoxyethylene-polyoxypropylene mono amine of approximately 1000 mol. wt.
All JEFFAMINE products are supplied by Texaco Chemical Co.

I claim:

1. A method for improving the anti-caking properties of triethylenediamine which comprises admixing with the triethylenediamine an effective amount of an additive comprising oxyalkylene amines and their amides, the amines comprising compounds of the formula:

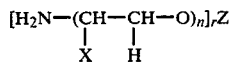

wherein X is a methyl radical, Z is a hydrocarbon radical having from 2 to 5 carbon atoms forming from 2 to 4 external ether linkages; n is a number from 1 to about 40 and r is a number from 2 to 4.

2. A method as in claim 1 where X is a methyl radical, n is a number from 2 to 17, Z is a 1,2-propylene radical and r is about 2 or 3.

3. A method as in claim 1 where the compound comprises a polyoxypropylene diamine of about 230 molecular weight.

4. A method as in claim 1 where the compound comprises a polyoxypropylene diamine of about 400 molecular weight.

5. A method as in claim 1 where the compound comprises a polyoxypropylene diamine of about 2000 molecular weight.

6. A method as in claim 1 where the compound comprises a polyoxypropylene triamine of about 400 molecular weight.

7. A composition comprising triethylene diamine with an amount of an additive effective for improving the anti-caking properties of the composition, the additive comprising compounds of the formula:

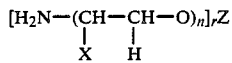

wherein X is a methyl radical, Z is a hydrocarbon radical having from 2 to 5 carbon atoms forming from 2 to 4 external ether linkages; n is a number from 1 to about 40 and r is a number from 2 to 4.

* * * * *